United States Patent [19]

Seitz

[11] Patent Number: 5,088,503

[45] Date of Patent: Feb. 18, 1992

[54] METHOD AND APPARATUS FOR THE PRODUCTION OF INSERTS

[76] Inventor: Peter Seitz, Moehlstrasse 29, Munchen 80, Fed. Rep. of Germany

[21] Appl. No.: 335,207

[22] PCT Filed: May 19, 1988

[86] PCT No.: PCT/EP88/00444

§ 371 Date: Jan. 16, 1990

§ 102(e) Date: Jan. 16, 1990

[87] PCT Pub. No.: WO88/09147

PCT Pub. Date: Dec. 1, 1988

[30] Foreign Application Priority Data

May 21, 1987 [DE] Fed. Rep. of Germany ....... 3717126

[51] Int. Cl.⁵ .............................................. A61B 5/103
[52] U.S. Cl. .................................... 128/779; 12/142 N
[58] Field of Search ......................... 128/774, 779, 782; 12/142 N, 146 M, 146 L; 33/791, 832, 833

[56] References Cited

U.S. PATENT DOCUMENTS

| | | | |
|---|---|---|---|
| 3,696,456 | 10/1972 | Dunham et al. | 12/146 L |
| 4,195,643 | 4/1980 | Pratt | 128/779 |
| 4,517,696 | 5/1985 | Schartz | 128/779 |
| 4,745,290 | 5/1988 | Frankel et al. | 12/146 L |
| 4,876,758 | 10/1989 | Rolloff et al. | 128/779 |

Primary Examiner—Max Hindenburg
Attorney, Agent, or Firm—Burgess, Ryan & Wayne

[57] ABSTRACT

A method for the production of inserts or the like is shown, with a patient or also a healthy person standing-/walking/sitting/lying/biting in a defined position and-/or movement with the body part to be fitted (foot, buttocks/back, teeth) on/over an electronic measuring arrangement for two- or three-dimensional measurement of the forces (pressures) acting on the measuring arrangement. The output signals of the measuring arrangement corresponding to the pressure-force distribution under the body part in the two- or three-dimensional pattern of the pressure-force distribution are relayed to a computer and compared with a stored set of desired values (wanted or ideal data). The differences between the distribution patterns are transformed into control signals for controlling an apparatus for the manufacture of the inserts or seating furniture surfaces, lounging furniture surfaces, dental prostheses, in such a way that upon addition of the (virtual) pressure force compensation distribution in accordance with the form (height) and/or rigidity of the inserts or the like to be manufactured to the actual pressure force distribution pattern, the desired pressure force distribution pattern essentially results.

15 Claims, 3 Drawing Sheets

METHOD AND APPARATUS FOR THE PRODUCTION OF INSERTS

BACKGROUND OF THE INVENTION

The invention relates to a method and apparatus for measuring parameters, and has particular applicability to the production of shoe inserts and the like.

The term "inserts" is to be understood here as a generic term for technical objects which are brought into force-locking and/or form-locking union with parts of the human body. A typical example are orthopedic inserts or insoles which are to be adapted to the foot of a patient, and also, of course, of healthy persons. Also involved is seating or lounging furniture which is to be adapted to the respective body parts of the user. Also it means prostheses or ortheses which are to he adapted to the stump of a limb. Further the invention also involves the adaptation of dental prostheses (full prostheses as well as single teeth or crowns) which are to be adapted, especially taking into consideration the movement geometry of the chewing apparatus, to the opposite (natural or likewise artificial) teeth.

In making orthopedic inserts (and also e.g. prostheses or corsets) present practice is to perform a (three-dimensional) survey of the forms to be adapted or to be corrected. This survey can take place through impressions in thermosetting compounds or by direct (optical) surveying. In any case, therefore, one proceeds practically exclusively from three-dimensional contours, and moreover generally in the unstressed state of the respective body part.

It has now been found that inserts, prostheses or also seating or lounging furniture made on the basis of these surveys are often felt by the user to be unpleasant, annoying, etc. Moreover, the correction results are not optimal. Lastly, in particular in the case of inserts/insoles, the problem exists that in many points the orthopedic shoemaker works "on intuition", so that the inserts made by him are not readily to be manufactured on the basis of purely objective test data. When making dental prostheses the procedure is still more inaccurate, again simply a direct survey of the three-dimensional contours taking place, namely by way of impressions in plastic compounds and subsequent grinding down of "pressure spots" which appear on the dental prosthesis when biting on dyed paper.

OBJECTS AND SUMMARY OF THE INVENTION

Starting with the above stated prior art, it is an object of the present invention to develop a method and an apparatus of the initially mentioned kind to the effect that at little cost improved results (with respect to corrections, compatibility, etc.) can be obtained in a satisfactorily reproducible manner.

This problem is solved by the present invention. In particular that the force distribution or respectively the two- or three-dimensional pattern of the occurring forces is made use of to produce the inserts, seating furniture surfaces etc., and this in such a way that direct control of the machine manufacturing the parts becomes possible. By direct control must be understood here also the case as an inferior form of realization where a conformable reproduction of the object to be manufactured is produced by the computer and then (although somewhat laboriously) the object is made according to this conformable reproduction. Comprised here also is the printout of corresponding sets of test data. In all cases, however, satisfactory factory reproducibility of the method results, whereby the quality of the resulting product is increased and at the same time the costs are reduced.

The manufacture of orthopedic inserts can here occur so that the computer-generated control data control a numerically controlled machine for the manufacture of the insert itself. This can be done e.g. by mill cutting, by appropriate hot or cold shaping with respect to the geometric dimensions, an approximation to the "ideal" pressure pattern being produced by the respective shaping, or excessive pressures at certain points being absorbed or compensated (e.g. by depressions in the insert). If the adaptation of prostheses is involved, it is possible by the evaluation of the pressure pattern to achieve optimum adaptation of the denture or of the chewing surfaces to the movement geometry of the chewing apparatus, which at present is possible only by very complicated three-dimensional surveying. In particular there are taken into consideration in this case also three-dimensional test data, that is, shear forces acting at the chewing surfaces.

Another possibility within the invention is to determine, by numerical control, only or additionally the hardness or rigidity of the material of which the inserts or seating surfaces etc. are made. Site-dependent adjustment of e.g. the composition of a plastic of which the inserts (or mattress) are made or with which a chair blank is covered, site-dependent determination of the degree of foam expansion, site-dependent control of the setting of a hardenable plastic, site-dependent adjustment of the density of the material (e.g. by drilling or pressing) etc. is then possible.

In a further, preferred embodiment of the invention, there is determined in addition to the force distribution, at least in the regions in which the foot does not rest on the measuring platform under load, the distance of the foot sole portions not in bearing contact from the measuring platform, thus obtaining additional information for shaping the insert in the sense of a compensation of "error forms" and transmitting it to the insert-making machine.

If, instead of inserts, e.g. a chair or a motor vehicle seat is to be constructed, one proceeds advantageously, not from a flat measuring platform, but from a "standard chair" or blank, whose surfaces lying opposite the body are equipped with respective force-measuring pickups (and preferably distance pickups in addition). When a patient sits on such a blank, there results in the measurement an "error pattern", on the basis of which (taking into consideration the forms of the blank) the numerically controlled machine can then produce the seat cushion actually to be fitted to the subject. The same applies, of course, also to the fitting of prostheses. Here, too, therefore, what is involved is essentially the measurement of forces, their comparison with a set of desired values, and the automatic and hence exactly reproducible production of seating furniture/prostheses/ortheses, after the computation of respective control signals, through numerically controlled machines.

The input of the control data into the machine for the production of the inserts, etc. need not occur on line; it may be carried out by hand, as has been described at the beginning. So also it is possible in principle, instead of using numerically controlled machines, to make e.g.

templates which serve for copying by hand. This inferior form of realization of the method is, of course, also comprised under the inventive idea.

BRIEF DESCRIPTION OF THE DRAWINGS

For better comprehension, preferred embodiments of the invention will be explained more specifically below with reference to the illustrations.

FIG. 2 is a side view of a measuring platform with a foot placed on:

DETAILED DESCRIPTION OF THE PREFERRED EMBODIMENTS

Figure 1:
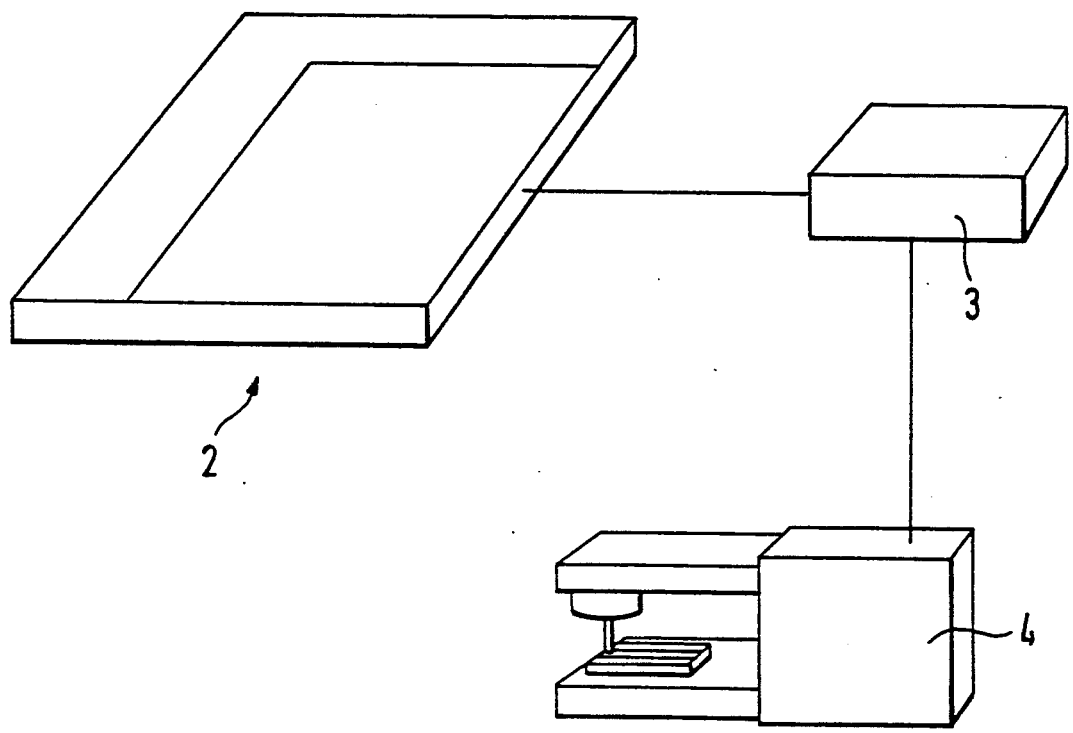
FIG. 1 is a schematic layout of an apparatus for carrying out the method according to the invention.

As shown in FIG. 1, a measuring platform 2 is connected to a computer 3, the output of which controls a numerically controlled milling cutter (drilling machine, etc.). This device for the production of the inserts (prostheses etc.) is provided with the reference number 4.

Preferably there are carried out not only purely static measurements, but the patient is made to run over the measuring platform 2 several times, the resulting pressure distribution pattern being averaged. In so doing, a correlation of the instantaneously measured "pressure pattern" with the previously measured pressure pattern is made with respect to the position of the measurement plane. By this averaging a substantial improvement of the insert fit is possible, as the actual pressure pattern is derivable not only with increased accuracy but also with exclusion of various falsifying influences (cramped body posture etc.). Furthermore a "dynamic" measurement is effected, which surprisingly gives much more information about the actual errors in the pressure pattern (as compared with a "normal" pressure pattern) than the purely static measurement. Many different platforms may be used, and among others, the system sold under the name of "EMED", reported e.g. in "Arzt heute", page 3 (Oct. 16, 1985) can be used. Other types of locus-resolving measuring platforms or measuring surfaces can be used as well.

Instead of a rigid platform 2 there may be used (as also for the production of prostheses/corsets) a flexible measuring mat which (cut out in the form of an insert sole) can be placed in a shoe. The pressure distribution pattern measurable while the subject walks (runs, stands) is then also influenced by the shoe itself, so that an additional adaptation of an insert or insole to the shoe can also take place. In particular for the production of foot pads (for given shoes) this is of advantage. Further it is possible to provide additionally also a "standard insert" between shoe and measurement insert, which is then correctable with reference to the measurement data obtained and is thus adaptable to the foot and shoe simultaneously.

Figure 2:
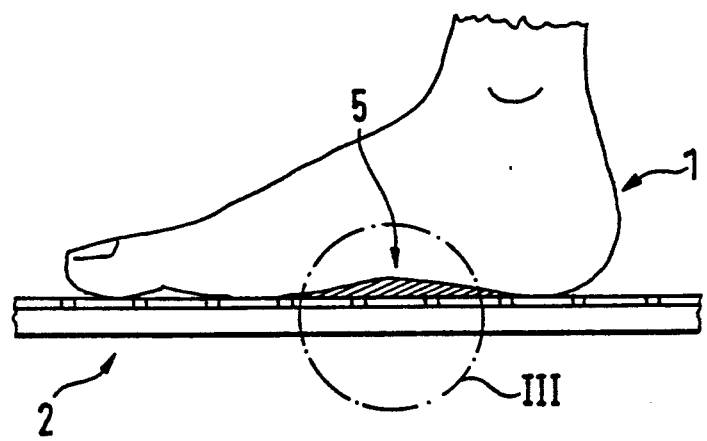
Figure 3:
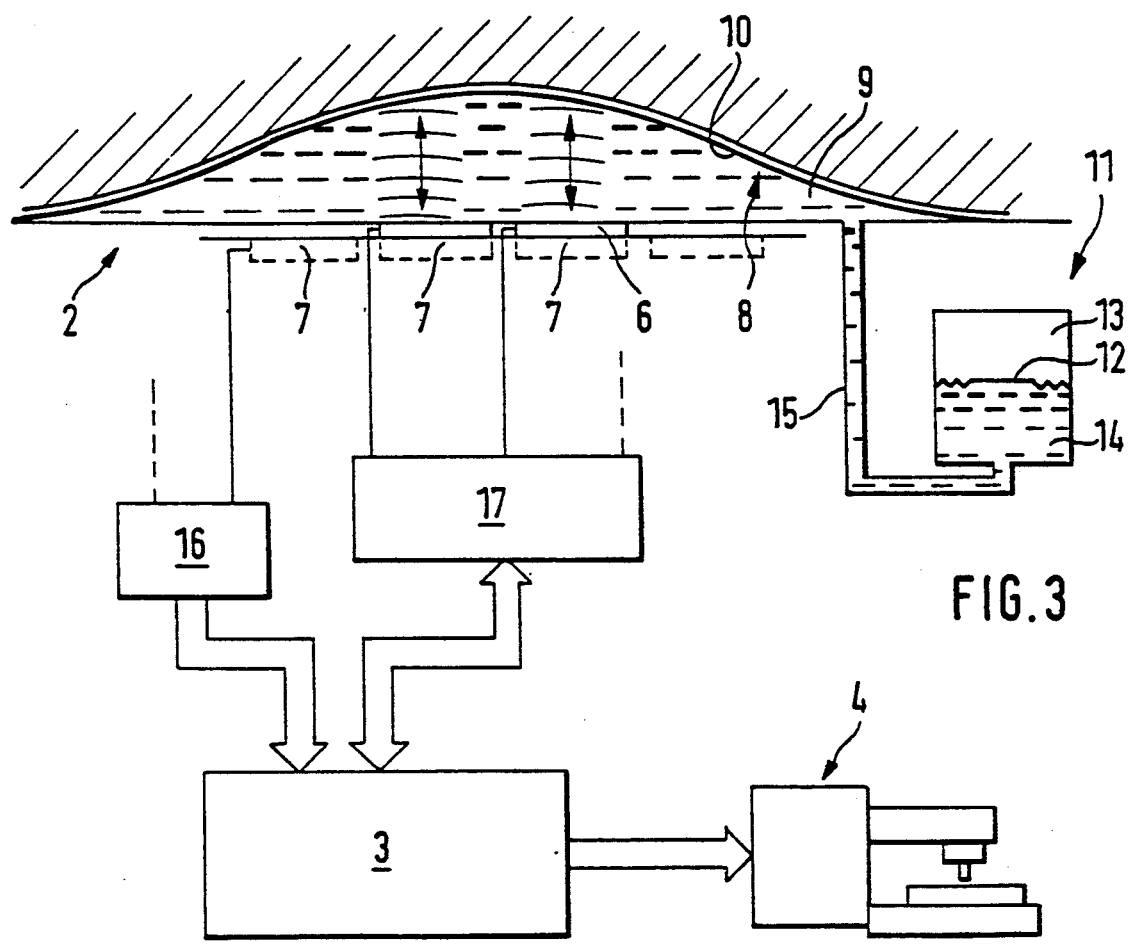
FIG. 3 is a basic representation of the area labeled III in FIG. 2.

FIG. 2 illustrates a foot 1 placed on a measuring platform 2, in side view. On the measuring platform 2 are shown schematically further the data pickups, e.g. capacitive pickups. It is evident from this illustration that in the region between heel and forefoot a region 5 exists in which the foot (except for an extreme flat foot) rests on the measuring platform 2 or respectively on the surface thereof. This region III is now measured ("metered") preferably with respect to its geometric dimensions in addition to the pressure distribution measurement, to be able to manufacture the insert (prosthesis, corset) accordingly. A preferred form of realization of an arrangement for the measuring of such spaces is shown in FIG. 3.

Here, close to the surface of the measuring platform 2, a foil (film) 10 is applied which with the surface of the measuring platform 2 can form a cavity which through a conduit 15 can be filled with a liquid 9. To this end the conduit 15 communicates with a pressure-generating unit 11 which in the example shown in FIG. 3 comprises a space 13 filled with compressed gas, which space is separated by a diaphragm 12 from a reservoir 14 for liquid 9. If the volume is made large enough, this arrangement acts so that a pressure largely independent of the geometric dimensions prevails in the liquid 9, so that the foil 10 presses onto the foot sole with constant force.

On the surface of the measuring platform 2 or respectively substantially directly on the sensors 7, piezoelectric transducers 6 are arranged, which are connected to the computer 3 via an actuating and evaluating circuit 17. The piezoelectric transducers 6 transmit (pulsed) ultrasonic signals (arrows in FIG. 3), which are reflected by the foil surface 10 and received by the same (possibly by additional) piezoelectric transducers and relayed to the evaluating circuit 17. From the transit time differences the distance of foil 10 and hence of the foot sole in the region not making contact is measurable. Preferably the transducers 6 are designed as piezoelectric foil which are contacted on both sides through conductor runs arranged in matrix form. Thereby a separate activating and/or polling of the transducers is possible to obtain a three-dimensional pattern. Further it is of advantage if several piezoelectric transducers 6 are combined to obtain a directional characteristic, thereby further improving the locus resolution of this measurement arrangement. By the liquid filling very high frequencies, a very high resolution is possible; and the sensitivity of the system increases due to the low attenuation in the liquid.

In another preferred embodiment of the invention not shown here, inductive or capacitive pickups are provided instead of piezoelectric transducers 6, in which case the foil 10 is then preferably metallized.

Figure 4:
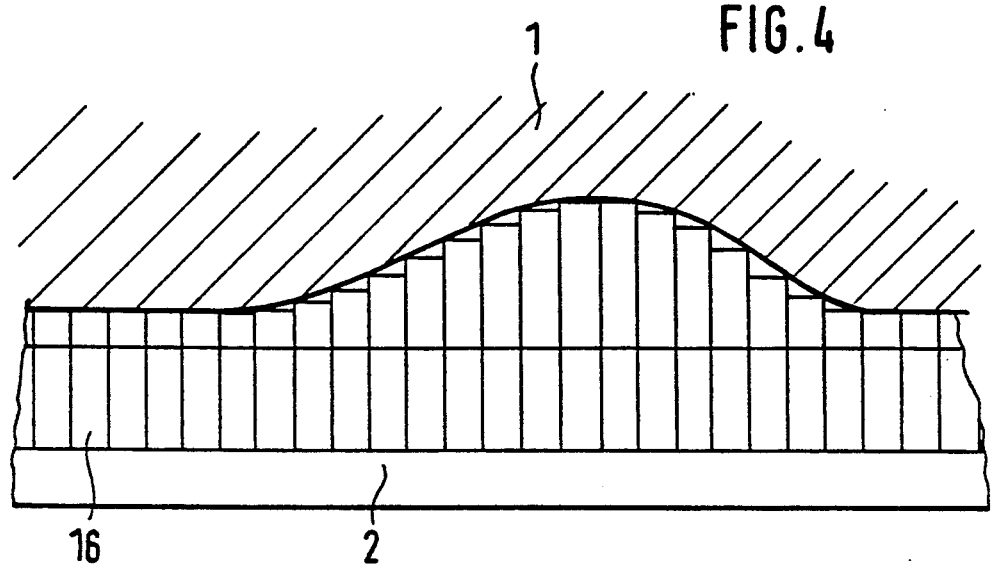
FIG. 4 is a further preferred form of realization of a distance measuring device.
Figure 5:
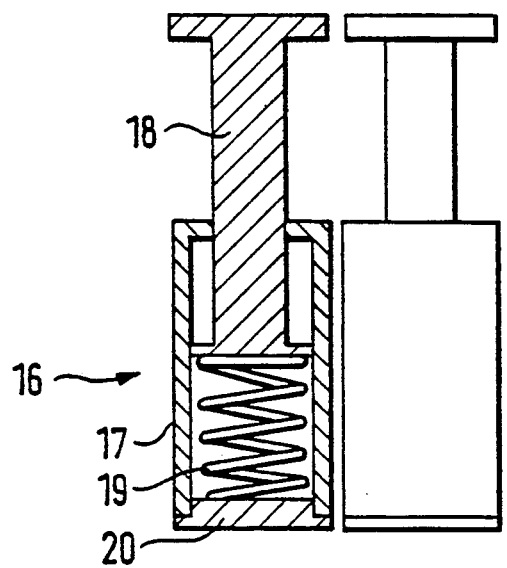
FIG. 5 is a detail of a single distance-measuring pickup from FIG. 4.

In the form of realization shown in FIG. 4, the distance between the measuring platform 2 and foot 1 is measured through a spring-ram arrangement, which are applied standing side by side on a rigid platform 2 and uniformly covering the measurement surface thereof. Each spring ram 16 (also shown diagrammatically in FIG. 3) comprises a housing 117, in which a ram 18 telescopes. Each ram 18 is pushed away from the platform 2 by a spring 19, its seating being formed by a cover 20 in the housing 117. The strength of the springs 19 is made so low that where the foot, when standing, rests on a flat, hard support, the springs 19 are completely compressed. Only in the regions in which, due to its form, the foot is spaced from a flat, hard platform, the rams 18 are extended. Each ram 18 then exerts through the spring 19 and the bottom 20 a force on the measuring platform 2, the amplitude of which is inversely proportional to the length of the spring 19 and hence proportional to the distance of the respective foot section from the area defined by the completely pressed-in rams. By measuring these forces, therefore, the distances can be determined at the same time.

The arrangements shown in FIG. 2 to 5 can serve also for optimum design of lounging furniture. In a preferred embodiment of the invention, not shown in the illustrations, one proceeds however, for the production of lounging or seating furniture, from a blank, the form of which is adapted to average values. Such blanks are then provided with an arrangement of pressure force pickups 7. For the production of prostheses the equivalent applies.

For the production of dental prostheses is suitable in particular a flexible measuring arrangement (as can be used e.g. also as insert sole as described above) the small thickness being of importance here to avoid impermissible falsification of the movement geometry of the chewing apparatus by the measuring arrangement.

I claim:

1. A method for the production of inserts and the like for a person, comprising the steps of:
   electronically measuring a spatial pattern of forces applied by the person to a measuring arrangement;
   producing output signals in correspondence with said measured forces;
   supplying said output signals to a computer;
   comparing said supplied output signals in the computer with stored signals corresponding to a stored set of desired values of a force distribution pattern;
   producing control signals in response to differences between said output signals and said stored signals;
   controlling apparatus for making the inserts and the like in response to said control signals such that a desired force distribution pattern results.

2. A method according to claim 1; further including the step of applying said forces to a portion of said measuring arrangement by contact of the person with a surface of the measuring arrangement in which a portion of said surface is not contacted by the person; and said step of electronically measuring includes the step of 3-dimensionally scanning distances between said person and portions of said surface of the measuring arrangement that are not contacted by the person by means of distance sensors; said step
   of producing output signals includes the step of producing output signals by said sensors such that the output signals correspond to a distance pattern between the person and the measuring arrangement and said stored set of desired values correspond to a desired distance pattern.

3. A method according to claim 1; wherein said output signals are averaged over a plurality of measurements as varying forces are applied by the person to the measuring arrangement.

4. A method according to claim 1; wherein said step of controlling includes a step of controlling the apparatus so as to control the height and/or rigidity of the inserts and the like in accordance with a conformable reproduction of the stored set of desired values.

5. Apparatus for making inserts and the like for a person, said apparatus comprising:
   electronic measuring a spatial pattern of means for measuring forces thereon; and for producing output signals in correspondence with said measured forces;
   computer means including storage means for storing stored signals corresponding to a stored set of desired values of a force distribution pattern and comparison means for producing control signals in response to differences between said output signals and said stored signals and for controlling apparatus for making the inserts and the like in response to said control signals such that a desired force distribution pattern results.

6. Apparatus according to claim 5; wherein said electronic measuring means includes a surface on which forces are applied by a person and a plurality of distance sensor means for 3-dimensionally scanning distances between a body part of the person and the surface of the measuring means to produce said output signals, said plurality of distance sensor means being connected to the computer means.

7. Apparatus according to claim 6; wherein said distance sensor means are effectively provided directly on the surface of the measuring means.

8. Apparatus according to claim 6; wherein said distance sensor means include contactless measuring sensors.

9. Apparatus according to claim 8; wherein said distance sensor means are one of capacitance and inductance sensors which measure the transit time of one of reflective light and ultrasonic waves.

10. Apparatus according to claim 5; wherein said measuring means include a matrix arrangement of force pickup means for measuring said forces.

11. Apparatus according to claim 5; wherein an arrangement for application of defined forces to body part regions of the person is provided between the measuring means and the sole of a foot of the person not in contact with the surface of the measuring means.

12. Apparatus according to claim 11; wherein said arrangement for application of defined forces includes a foil applied tightly on the surface of the measuring means; at least one conduit means for supplying fluid to a space between said foil and said surface of the measuring means and pressure generating means for supplying fluid under pressure through said at least one conduit means to said space such that the foil applies a force essentially completely on a body part to be measured; and wherein said distance sensor means include ultrasonic sensors for radiating ultrasonic waves directly into the fluid-filled space between the foil and the surface of the measuring means.

13. Apparatus according to claim 12; wherein said ultrasonic distance sensors include a matrix array of piezoelectric foil having surfaces which are contacted via crossing conductor runs and are excited and/or polled via a multiplexer arrangement.

14. Apparatus according to claim 5; wherein said apparatus for making inserts and the like includes a CNC milling cutter for the production of pourable molds and/or deep drawing molds.

15. Apparatus according to claim 5; wherein said apparatus for making inserts and the like includes a plastic molding machine to which control signals for sight-dependent adjustment of material rigidity are suppliable.

* * * * *